US011318152B2

(12) United States Patent
Yada et al.

(10) Patent No.: US 11,318,152 B2
(45) Date of Patent: May 3, 2022

(54) PHARMACEUTICAL AGENT FOR IMPROVING AUTISM SPECTRUM DISORDER AND MENTAL DISEASE

(71) Applicant: MATSUTANI CHEMICAL INDUSTRY CO., LTD., Itami (JP)

(72) Inventors: Toshihiko Yada, Kokubunji (JP); Yusaku Iwasaki, Kyoto (JP); Shigetomo Suyama, Abiko (JP)

(73) Assignee: MATSUTANI CHEMICAL INDUSTRY CO., LTD., Itami (JP)

( * ) Notice: Subject to any disclaimer, the term of this patent is extended or adjusted under 35 U.S.C. 154(b) by 0 days.

(21) Appl. No.: 16/964,910

(22) PCT Filed: Jan. 26, 2018

(86) PCT No.: PCT/JP2018/002549
§ 371 (c)(1),
(2) Date: Jul. 24, 2020

(87) PCT Pub. No.: WO2019/146082
PCT Pub. Date: Aug. 1, 2019

(65) Prior Publication Data
US 2021/0038621 A1 Feb. 11, 2021

(51) Int. Cl.
A61K 31/7004 (2006.01)
A61K 9/00 (2006.01)

(52) U.S. Cl.
CPC ........ *A61K 31/7004* (2013.01); *A61K 9/0053* (2013.01)

(58) Field of Classification Search
CPC .................................................. A61K 31/7004
See application file for complete search history.

(56) References Cited

U.S. PATENT DOCUMENTS

| | | | |
|---|---|---|---|
| 2005/0245459 A1 | 11/2005 | Izumori et al. | |
| 2010/0143485 A1 | 6/2010 | Hudnut et al. | |
| 2011/0112043 A1 | 5/2011 | Izumori et al. | |
| 2016/0346304 A1 | 12/2016 | Yada et al. | |
| 2018/0296582 A1* | 10/2018 | von Maltzahn | A61P 31/00 |

FOREIGN PATENT DOCUMENTS

| | | | |
|---|---|---|---|
| JP | 2005-263734 A | | 9/2005 |
| JP | 2007-525442 A | | 9/2007 |
| JP | 5330976 B2 | | 8/2013 |
| JP | 2014084291 A | * | 5/2014 |
| JP | 2014-171392 A | | 9/2014 |
| JP | 2015-164900 A | | 9/2015 |
| JP | 2018-27896 A | | 2/2018 |

OTHER PUBLICATIONS

Matsuo et al., Asia Pacific J. Clin. Nutr., "Metabolic effects of D-psicose in rats: studies on faecal and urinary excretion and caecal fermentation", 2003, vol. 12, No. 2, pp. 225-231 (Year: 2003).*
Translation of JP2014084291, Tanaka et al., published May 2014, 6 pages. (Year: 2014).*
Office Action dated Jun. 25, 2020 issued in corresponding Japanese Application No. 2016-159203.
Bales, et al., "Long-term exposure to intranasal oxytocin in a mouse autism model", Translational Psychiatry, vol. 4, No. e480, pp. 1-10, 2014.
Blevins, et al., "Translational and therapeutic potential of oxytocin as an anti-obesity strategy: Insights from rodents, nonhuman primates and humans", Physiol Behav., vol. 152 (pt B), pp. 438-449, 2015.
Egashira, et al., "New Topics in Vasopressin Receptors and Approach to Novel Drugs: Role of the Vasopressin Receptor in Psychological and Cognitive Functions", Journal of Pharmacological Sciences, vol. 109, pp. 44-49, 2009.
Huang, et al., "Chornic and Acute Intranasal Oxytocin Produce Divergent Social Effects in Mice", Neuropsychopharmacology, vol. 39, pp. 1102-1114, 2014.
Koshimizu, et al., "Vasopressin V1a and V1b Receptors: From Molecules to Physiological Systems", Physiol. Rev., vol. 92, pp. 1813-1864, 2012.
Hollander, et al., "Oxytocin Infusion Reduces Repetitive Behaviors in Adults with Autistic and Asperger's Disorders", Neuropsychopharmacology, vol. 28, pp. 193-198, 2003.
Yatawara, et al., "The effect of oxytocin nasal spray on social interaction deficits observed in young children with autism: a randomized clinical crossover trial", Molecular Psychiatry, vol. 21, pp. 1225-1231, 2016.
Watanabe, et al., "Clinical and neural effects of six-week administration of oxytocin on core symptoms of autism", Brain, vol. 138, pp. 3400-3412, 2015.
Egashira, et al., "The role of vasopressin receptors in mental function", Journal of Pharmacological Sciences, vol. 134, pp. 3-7, 2009.

(Continued)

*Primary Examiner* — Bahar Craigo

(74) *Attorney, Agent, or Firm* — Nath, Goldberg & Meyer; Joshua B. Goldberg

(57) ABSTRACT

An object of the present invention is to provide a novel pharmaceutical agent for improving autism spectrum disorder, a pharmaceutical agent for improving a mental disease, or a supplement exerting an effect of improving social behaviors or developing sociality or an anti-anxiety and anti-stress effect or a functional food exerting such an effect. The present invention also provides a pharmaceutical agent for promoting the secretion of oxytocin and/or vasopressin in the brain. The above objects are achieved by a pharmaceutical agent for improving autism spectrum disorder, a pharmaceutical agent for improving a mental disease, or a supplement exerting an effect of improving social behaviors or developing sociality or an anti-anxiety and anti-stress effect or a functional food exerting such an effect, or a pharmaceutical agent for promoting the secretion of oxytocin and/or vasopressin, which comprises D-allulose as an active ingredient.

20 Claims, 9 Drawing Sheets

(56) References Cited

OTHER PUBLICATIONS

Meyer-Lindenberg, et al., "Oxytocin and vasopressin in the human brain: social neuropeptides for translational medicine", Nature Review Neuroscience, vol. 12, No. 9, pp. 524-538, 2011.

Silverman, et al., "Behavioural phenotyping assays for mouse models of autism", Nature Review Neuroscience, No. 11. No 7, pp. 490-502, 2010.

Office Action dated Dec. 24, 2020 issued in corresponding Japanese Application No. 2016-159203.

Unno, "Aging Acceleration under Psychosocial Stress and Anti-stress Effect of Theanine", Basic Aging Research, vol. 35, No. 4, pp. 9-15.

\* cited by examiner

New region 3 g/kg
D-allulose, oral administration

200 μm 3 g/kg
D-allulose, oral administration

100 μm 3 g/kg D-allulose, oral administration 1 g/kg, oral administration 3 g/kg, oral administration

PHARMACEUTICAL AGENT FOR IMPROVING AUTISM SPECTRUM DISORDER AND MENTAL DISEASE

This is a National Phase Application filed under 35 U.S.C. 371 as a national stage of PCT/JP2018/002549, filed Jan. 26, 2018, the content of which is hereby incorporated by reference in its entirety.

TECHNICAL FIELD

The present invention relates to a pharmaceutical agent for promoting the secretion of oxytocin and/or vasopressin. The present invention also relates to a pharmaceutical agent for improving autism spectrum disorder or a pharmaceutical agent for improving a mental disease as well as a pharmaceutical agent for improving social behaviors or developing sociality, or a supplement or a functional food exerting an anti-anxiety and anti-stress effect.

BACKGROUND ART

Autism spectrum disorder (ASD) is a classification of various neurodevelopmental disorders in Diagnostic and Statistical Manual of Mental Disorders, 5th Edition (DSM-5). ASD is characterized by two cardinal symptoms, that is, persistent deficits in social communications and interrelationships as well as limited reciprocal behaviors, interests, and activities, and includes spectra ranging from mild to severe.

As pharmaceutical agents for treating ASD, central nervous system stimulants, antipsychotic agents, antiepileptic agents, selective serotonin reuptake inhibitor, and the like are prescribed as symptomatic treatments depending on the symptoms. However, the current situation is that there is no effective pharmaceutical agent for improving the cardinal symptoms.

Oxytocin is a peptide hormone generated in the hypothalamus of the brain and is known to have uterine contraction stimulation and lactation stimulation effects for inducing delivery. Recently, it has been suggested that oxytocin may potentially contribute to the onset of repetitive behaviors observed in the patients of autism spectrum disorder or ASD (for example, Non Patent Document 1), and it has been reported that social behaviors are improved in autism patients by the nasal drop administration of oxytocin (for example, Non Patent Documents 2, 3).

However, in the treatment using nasal drop administration of oxytocin, non-effective cases have also been reported, so its effect is definite. Since the nasal drop is a route of administration with a large amount of leak, this is possibly because the transfer of oxytocin in blood is unstable. In addition, only a trace amount of blood oxytocin can pass through the brain barrier, it is assumed that transfer of oxytocin to the brain is unstable and only a trace amount thereof can be transferred. Moreover, it cannot be said to be easy for autism patients themselves or their families to surely conduct nasal drop administration.

Vasopressin is, like oxytocin, a peptide hormone that is synthesized in the hypothalamus of the brain and secreted into the blood from the posterior pituitary, and is known to have antidiuretic and blood pressure raising effects. On the other hand, vasopressin, which functions as a neurotransmitter in the brain, is also known to be involved in mentation of schizophrenia, autism and the like, like oxytocin (Non Patent Documents 4, 5).

CITATION LIST

Non Patent Documents

Non Patent Document 1: Eric Hollander, et al., "Oxytocin Infusion Reduces Repetitive Behaviors in Adults with Autistic and Asperger's Disorders" Neuropsychopharmacology (2003) 28, 193-198

Non Patent Document 2: Yatawara, C. J., et al., "The effect of oxytocin nasal spray on social interaction deficits observed in young children with autism: a randomized clinical crossover trial." Molecular Psychiatry, (2016)

Non Patent Document 3: Watanabe, T., et al., "Clinical and neural effects of six-week administration of oxytocin on core symptoms of autism." Brain: a Journal of Neurology 138(11): 3400-12, (2015)

Non Patent Document 4: Egashira Nobuaki, et al., Journal of Pharmacological Sciences, 2009, 134, 3-7

Non Patent Document 5: Meyer-Lindenberg A. et al., "Oxytocin and vasopressin in the human brain: social neuropeptides for translational medicine." Nat Rev Neurosci. 2011, 12(9): 524-38

PATENT DOCUMENTS

Patent Document 1: Japanese Translation of PCT Application Publication No. 2007-525442

Patent Document 2: Japanese Patent Application Publication No. 2014-171392

SUMMARY OF INVENTION

Problems to be Solved by the Invention

An object of the present invention is to provide a pharmaceutical agent exerting an effect of promoting the secretion of oxytocin and/or vasopressin, and further to provide a pharmaceutical agent exerting an effect of promoting the secretion of oxytocin and/or vasopressin thus to be capable of treating autism spectrum disorder.

The present invention also has an object to provide a novel pharmaceutical agent effective in treating autism spectrum disorder. In addition, the present invention further has an object to provide a novel pharmaceutical agent for improving a mental disease.

A further object of the present invention is to provide a therapeutical agent for treating autism spectrum disorder that has overcome instability of nasal oxytocin administration and the like.

A further object of the present invention is to provide a pharmaceutical agent that is capable of activating central oxytocin and/or vasopressin neurons to thus treat autism spectrum disorder.

Another object of the present invention is to provide a supplement exerting an effect of improving social behaviors or developing sociality or an anti-anxiety and anti-stress effect, or a functional food exerting such an effect.

Means for Solution of the Problems

The present inventors found that when D-allulose, which is a rare sugar, was orally administered to mice, the social behavior was improved. In addition, the present inventors also found that the oral administration of D-allulose activated the hypothalamus to activate the oxytocin neurons and the vasopressin neurons in the paraventricular nucleus (PVN) and the supraoptic nucleus (SON) as well as other novel portions, and also facilitated the expression of oxytocin and vasopressin mRNAs in the hypothalamus. These results indicate that the oral administration of D-allulose activates the function of neurons to produce oxytocin and/or vasopressin, which are known to have social behavior improvement, anti-anxiety, anti-stress, learning facilitation, anti-obesity effects, and the like, or promotes the secretion of oxytocin and/or vasopressin, to improve autism spectrum disorder and exert an anti-anxiety, anti-stress effect.

Hence, the present invention provides a pharmaceutical agent for promoting the secretion of oxytocin and/or vasopressin, comprising D-allulose as an active ingredient.

In the above aspect, the pharmaceutical agent for promoting the secretion is preferably a pharmaceutical agent for oral-administration.

In the above aspect, the pharmaceutical agent for promoting the secretion is preferable because it is possible for the pharmaceutical agent for promoting the secretion to be administered without simultaneously taking sucrose or a sucrose-containing food when being administered.

In the above aspect, the pharmaceutical agent for promoting the secretion is preferable because the pharmaceutical agent for promoting the secretion is capable of activating oxytocin and/or vasopressin neurons in the brain or is capable of promoting the secretion of oxytocin and/or vasopressin.

The present invention also provides D-allulose for use in promoting the secretion of oxytocin and/or vasopressin.

The present invention also provides the following aspects:
<1> A pharmaceutical agent for improving autism spectrum disorder comprising D-allulose as an active ingredient.
<2> A pharmaceutical agent for improving a mental disease comprising D-allulose as an active ingredient.
<3> A pharmaceutical agent for developing sociality or improving social behaviors, comprising D-allulose as an active ingredient.
<4> An anti-anxiety agent comprising D-allulose as an active ingredient.
<5> An anti-stress agent comprising D-allulose as an active ingredient.
<6> An anxiety-reducing food comprising D-allulose as an active ingredient.
<7> A stress-reducing food comprising D-allulose as an active ingredient.
<8> A pharmaceutical agent for promoting the secretion of oxytocin and/or vasopressin, comprising D-allulose as an active ingredient.
<9> The pharmaceutical agent according to <1> or <2>, that promotes the secretion of oxytocin and/or vasopressin in the brain through oral administration of D-allulose, improving autism spectrum disorder or treating a mental disease.

In addition, the present invention provides the following:
<10> D-allulose for use in treating or improving the following disease or symptom:
(i) one or a plurality of diseases selected from the group consisting of autism spectrum disorder and mental diseases, and
(ii) one or a plurality of symptoms selected from the group consisting of social behavior disorders, anxiety disorders, and stresses.
<11> The D-allulose according to <10>, that is orally administered.
<12> The D-allulose according to <10> or <11>, for use in treating or improving the disease or symptom by promoting the secretion of oxytocin and/or vasopressin.

Furthermore, the present invention provides the following:
<20> A method for treating or improving the following disease or symptom, comprising administering an effective dose of D-allulose to a patient having the following disease or symptom:
(i) one or a plurality of diseases selected from the group consisting of autism spectrum disorder and mental diseases, and
(ii) one or a plurality of symptoms selected from the group consisting of social behavior disorders, anxiety disorders, and stresses.
<21> The method according to <20>, wherein D-allulose is orally administered.
<22> A method for treating or improving the following disease or symptom, comprising administering a pharmaceutical agent for promoting the secretion of oxytocin and/or vasopressin to a patient:
(i) one or a plurality of diseases selected from the group consisting of autism spectrum disorder and mental diseases, and
(ii) one or a plurality of symptoms selected from the group consisting of social behavior disorders, anxiety disorders, and stresses, wherein
the pharmaceutical agent for promoting the secretion of oxytocin and/or vasopressin is D-allulose.
<23> The method according to <22>, wherein the D-allulose is orally administered.

Advantageous Effects of Invention

The pharmaceutical agent of the present invention makes it possible to promote secretion of oxytocin and/or vasopressin in the brain of a human or an animal.

The present invention makes it possible to provide an effective pharmaceutical agent for autism spectrum disorder. In addition, the present invention provides a further novel pharmaceutical agent for improving a mental disease.

Since the pharmaceutical agent of the present invention exerts the effects through oral administration, it is possible to provide a pharmaceutical agent for improving autism spectrum disorder that has overcome instability of administration routes like nasal oxytocin administration.

In addition, since the pharmaceutical agent of the present invention is capable of activating the central oxytocin neuron, it is possible to solve the problem of the nasal oxytocin administration in passing through the blood-brain barrier.

Another object of the present invention is to provide a supplement exerting an effect of improving social behaviors or developing sociality or an anti-anxiety and anti-stress effect, or a functional food exerting such an effect.

In addition, the present invention makes it possible to provide a pharmaceutical agent that has no problem in safety or side effects, that can be orally administered, and that is easy for children to take because the pharmaceutical agent has sweetness.

DESCRIPTION OF EMBODIMENTS

D-Allulose

Figure 1A:
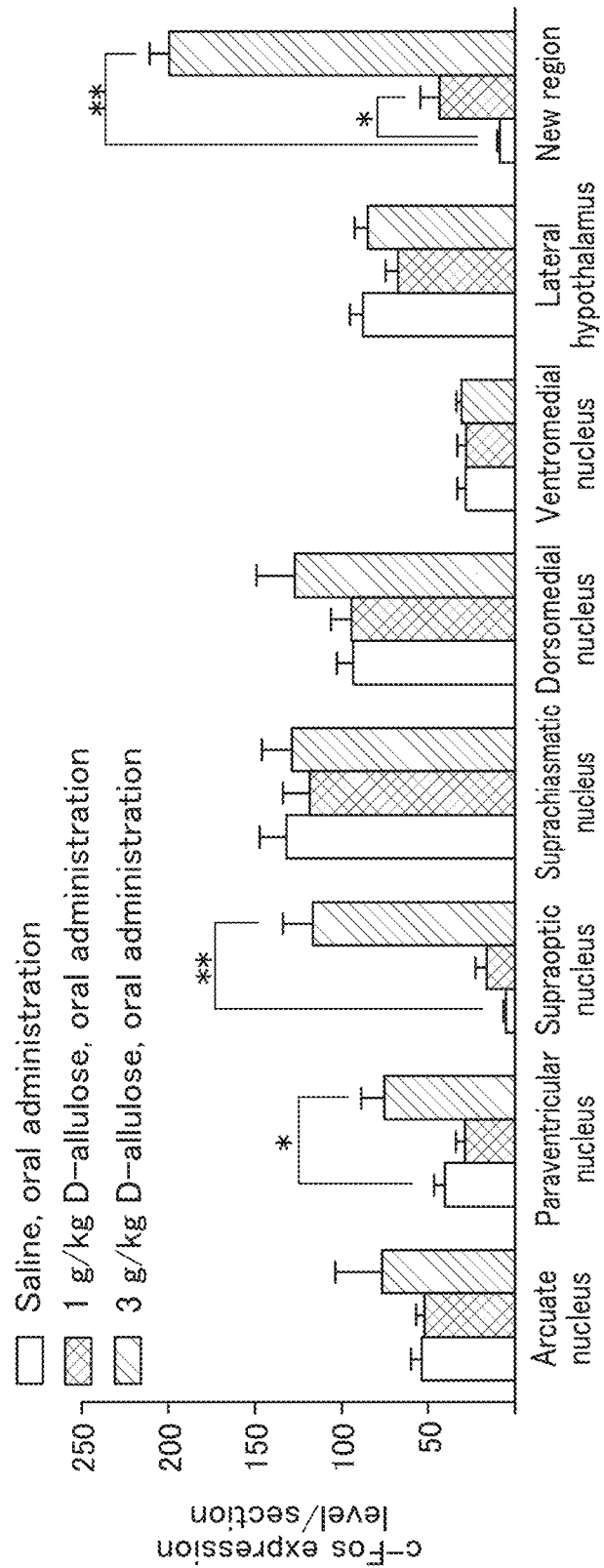
FIG. 1A illustrates that the oral administration of the pharmaceutical agent of the present invention significantly facilitated the c-Fos expression level particularly in the paraventricular nucleus (PVN), the supraoptic nucleus (SON), and a new region of the hypothalamus.
Figure 1B:
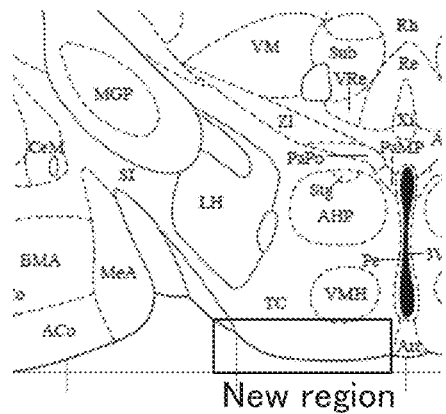
FIG. 1B illustrates the atlas of the mouse hypothalamus (Bregma—1.22 mm). In addition, the new region that is focused in the present invention and does not have a region name is illustrated with a rectangular frame in FIG. 1B.
Figure 1C:
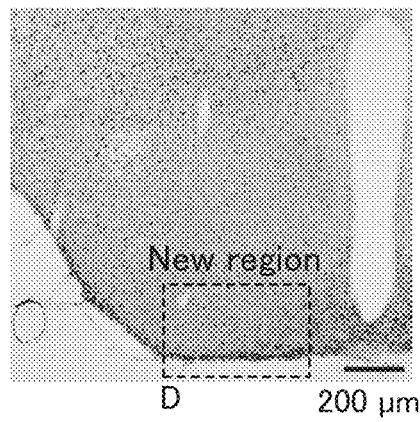
FIG. 1C illustrates a photomicrograph of the mouse hypothalamus section of a c-Fos immunostained after the oral administration of the agent of the present invention. The c-Fos positive (black dot) cells are observed in a region indicated by new region in FIG. 1C.
Figure 1D:
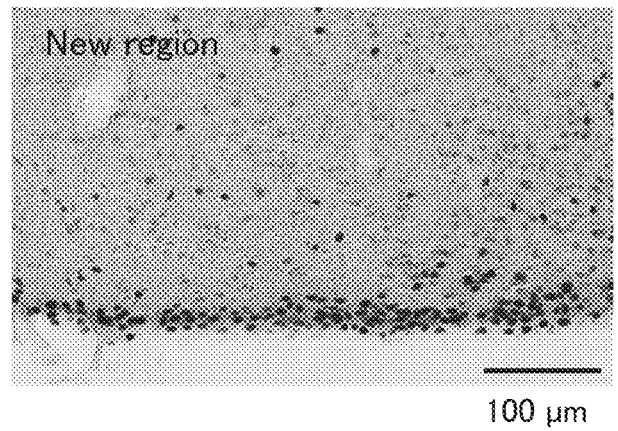
FIG. 1D is an enlarged diagram of the new region portion in FIG. 1C.

D-allulose, which is an active ingredient of the pharmaceutical agent, the supplement, and the functional food of the present invention, is one of monosaccharides classified into hexose and ketose. In addition. D-allulose is also called a rare sugar. D-allulose is a degree of sweetness of about 70% of that of sugar, and has an elegant and fresh sweetness similar to that of D-fructose, but the calorie of D-allulose is almost zero D-allulose has conventionally been publicly-known and may be used in any product no matter from which or in what form the product is. That is, regardless of the degree of purification, there are those extracted from plants such as *Itea*, those isomerized by the alkali-isomerization method using D-glucose or D-fructose as a raw material (for example, "Rare Sugar Sweet" produced by Matsutani Chemical Industry Co., Ltd.), those isomerized by the enzyme method utilizing enzymes (isomerase, epimerase, and the like) obtained from a microorganism or its recombinant using a D-glucose or D-fructose as a raw material (for example, "Astraea Allulose" produced by Matsutani Chemical Industry Co., Ltd.), and the like, so D-allulose can be relatively easily obtained.

In order for the pharmaceutical agent of the present invention to exhibit its effects, it is particularly preferable to orally take D-allulose. D-allulose can be used solely, and there is no need to take D-allulose together with sucrose or a sucrose-containing food or to administer D-allulose after taking these.

Pharmaceutical Agent•Supplement

The formulation of the pharmaceutical agent and supplement of the present invention is not particularly limited and may be, for example, any of liquid, tablet, granular, powder, capsule, gel, and sol formulations. In addition, the pharmaceutical formulation may be prepared in accordance with a publicly-known method, and may be conducted by mixing D-allulose as an active ingredient with a pharmaceutically acceptable carrier such as starch and carboxymethyl cellulose and adding a stabilizer, an excipient, a binder, a collapsing agent, and the like as necessary.

In addition, the administration is not limited to the oral administration but may be a parenteral administration using injection, a patch, a spray, or the like. Moreover, such a pharmaceutical agent may be prepared in combination with appropriate additives such as a generally-used excipient, a stabilizer, a preservative, a binder, a collapsing agent, and the like. Among the above-described forms of administering the pharmaceutical product, the oral administration is preferable.

Functional Food

The form of the functional food is not particularly limited, but D-allulose may be used, for example, for confectioneries such as pudding, jelly candy, chocolate, bread, cake, cookie, and bun with a bean-jam filling (manjuu), egg products such as fresh cream, beverages such as functional beverages, lactic acid beverages, fruit juice beverages, and carbonated beverages, favorite foods and beverages such as tea and instant coffee, dairy products such as ice cream, yogurt, and cheese, pastes such as flour paste, and syrup fruit, meat products such as ham, sausage, and bacon, processed seafood products such as fish ham, and fish sausage, and condiments such as soy sauce, sauce, and dressing.

In addition, D-allulose may also be used for a functional food or a nutrition supplement food such as a liquid food, an ingredient nutrition food, a drink nutrition food, and an enteral food. The form is not particularly limited, but, for example, in the case of a sports drink, nutritional additives and compositions such as amino acids, vitamins, and minerals, flavor, and dye may be blended in order to improve the nutrition balance and flavor.

Amount of Intake and Intake Method of D-Allulose

The amount of intake of the pharmaceutical agent, the supplement, and the functional food using D-allulose as an active ingredient of the present invention is not particularly limited as long as its effects can be obtained, but, for example, in the case of mice and rats, for each dose, the amount of D-allulose to be taken is preferably in the range of 0.07 g to 5.0 g, more preferably in the range of 0.1 g to 4.0 g, further preferably in the range of 0.15 g to 3.5 g, and still further preferably in the range of 1.2 g to 3.5 g, per 1 kg of the body weight.

For human, an amount of intake lower than the amount of intake for mice and rats may be used, and for example, an amount of approximately one-tenth may be used. For example, for each dose, the amount of D-allulose may be taken preferably in the range of 0.007 g to 0.5 g, more preferably in the range of 0.01 g to 0.4 g, further preferably in the range of 0.015 g to 0.35 g, and still further preferably in the range of 0.12 g to 0.35 g, per 1 kg of the body weight. The amount intake for a human is determined in consideration of the health status, body weight, age, and other conditions of the subject as well. For example, the amount of D-allulose taken once for one adult (60 kg) may be 10 g to 12 g (0.17 g to 0.2 g/kg). Moreover, the timing of intake is preferably before meal, further preferably within 1 hour before meal, and more preferably within 15 to 30 minutes before meal.

Other Additives

In a particular aspect, the second activator is an antipsychotic agent, an atypical antipsychotic agent, a pharmaceutical agent useful in treating the Alzheimer's disease, or a cholinesterase inhibitor.

In a particular aspect, the second activator is an antidepressant that includes SNRI (serotonin-noradrenaline reuptake inhibitor), SSRI (selective serotonin reuptake inhibitor), TCA (tricyclic antidepressant), and MAOI (monoamine oxidase inhibitor) but is not limited to these.

In a particular aspect, the second activator is lurasidone, olanzapine, risperidone, aripiprazole, amisulpiride, asenapine, blonanserin, clozapine, clothiapine, iloperidone, mosapramine, paliperidone, quetiapine, remoxipride, sertindole, sulpiride, ziprasidone, zotepine, pimavanserin, loxapine, donepezil, rivastigmine, memantine, galantamine, tacrine, amphetamine, methylphenidate, atomoxetine, modafinil, sertraline, fluoxetine, duloxetine, venlafaxine, phenelzine, selegiline, imipramine, desipramine, clomipramine, or L-DOPA.

The supplement and the functional food of the present invention may contain a water-soluble dietary fiber as an active ingredient besides D-allulose.

The water-soluble dietary fiber includes a high-viscosity dietary fiber such as pectin, glucomannan, alginic acid, guar gum, or agar or a low-viscosity dietary fiber such as indigestible dextrin, polydextrose, or a partially hydrolyzed guar gum.

Among these, from the viewpoint of their effects, particularly indigestible dextrin, partially hydrolyzed guar gum, polydextrose, and the like are preferable.

Among these, a low-viscosity dietary fiber is preferable from the viewpoint of its handling and shorter time taken to reach the large intestine. The low-viscosity water-soluble dietary fiber means a dietary fiber material that contains 50% by mass or more of a dietary fiber and is solved in water at ordinary temperature to become a solution having a low viscosity, generally, a solution exhibiting a viscosity of 20 mPas or less in a 5% by mass aqueous solution. The low-viscosity dietary fiber specifically includes indigestible dextrin, partially hydrolyzed guar gum, polydextrose (for example, Litesse and the like), a fiber derived from hemicellulose, and the like.

Indigestible dextrin is produced by heating and decomposing various starches, for example, potato starch, tapioca starch, corn starch, wheat flour starch, and the like at 130° C. or more and further hydrolyzing this with amylase, followed by decoloring and desalinating as necessary in accordance with a conventional method. The average molecular weight of the dietary fiber is approximately 500 to 3000, preferably 1400 to 2500, and further preferably around 2000. Indigestible dextrin is a dextrin with a developed branch structure in which the glucose residues have $\alpha$-1,4, $\alpha$-1,6, $\beta$-1,2, $\beta$-1,3, $\beta$-1,6-glucosidic bonds and part of the reducing terminal is levoglucosan (1,6-anhydroglucose). Indigestible dextrin is sold in the trade names of "NUTRIOSE" (produced by Roquette), "PINE FIBRE", "Fibersol 2" (produced by Matsutani Chemical Industry Co., Ltd.) ("SHOKUHIN SIN SOZAI FORUM (Advanced Food Ingredient Forum)" NO. 3 (1995, edited by Advanced Food Ingredients Council)).

Partially hydrolyzed guar gum is obtained by hydrolyzing guar gum with an enzyme, and its properties normally include low viscosity and cold water-solubility, its aqueous solution is neutral, colorless, and transparent. The partially hydrolyzed guar gum is sold in the trade name of "Sunfiber" (TAIYO KAGAKU Co., Ltd.), "Fiberon" (Dainippon Pharma Co., Ltd.).

The fiber derived from hemicellulose is normally produced by being derived from the hull of corn with alkali and then purified. The fiber derived from hemicellulose has a large average molecular weight of about 200,000, but has a low viscosity of approximately 10 cps in a 5% aqueous solution, and is dissolved in water to form a transparent liquid. The fiber derived from hemicellulose is sold in the trade name of "CELLACE" (Nihon Shokuhin Kako Co., Ltd.).

Polydextrose (Litesse) is obtained by polymerizing glucose and sorbitol in the presence of citric acid through liquid-pressure heating and is water-soluble with a low viscosity. Polydextrose (Litesse) is sold as "Litesse" (Pfizer).

Among these low-viscosity water-soluble dietary fibers, indigestible dextrin is most effective and preferable.

Pharmaceutical Agent for Improving Autism Spectrum Disorder

One aspect of the present invention is a pharmaceutical agent for improving autism spectrum disorder comprising D-allulose as an active ingredient.

Autism spectrum disorder (ASD) is a classification of various neurodevelopmental disorders in Diagnostic and Statistical Manual of Mental Disorders, 5th Edition (DSM-5). ASD is characterized by two concepts, that is, persistent deficits in social communications and interrelationships as well as limited reciprocal behavior, interest, and activity, and includes spectrum ranging from mild to severe.

The pharmaceutical agent of the present invention is a pharmaceutical agent for improving persistent deficits in social communications and interrelationships, which were classified as autism, Asperger syndrome, pervasive developmental disorder—not otherwise specified, childhood disintegrative disorder, and the like in previous DSM-IV (Diagnostic and Statistical Manual of Mental Disorders-IV).

Open Field Test

Tests for evaluating higher brain functions such as emotion and memory learning used for analyzing the phenotyping of gene-modified mice have conventionally been developed. These tests are used for disease analysis of ASD and development of therapeutic agent.

The open field test is a test that evaluates spontaneous activity, anxiety-like behavior, and the like in a novel environment by measuring the distance traveled, the number of rearings, the stereotyped behavior, the time spent in the center section, and the like under the novel environment. A mouse is placed in an open field, which is a novel and bright environment for a mouse, and is allowed to freely explore the open field for a certain period of time. The open field has a circular or square shape, and the size, in the case of a square, varies from a side of over 1 m to 30 cm or less. The experiment time is approximately 5 minutes in general, and significant overactivity, dormancy, and the like can be detected through observation for such a short period of time. In addition, a change in the behavior of an animal over time under a novel environment can be observed by recording for a long period of time. Since it is said that mice get accustomed to the open field environment by 30 minutes to approximately 2 hours, the experiment time is often set between 30 minutes to 3 hours. Also, the open field test is often used for analyzing the phenotyping of gene-modified mice and testing the reactivity to pharmaceutical agents.

Social Interaction Test

The sociality test (also called the social interaction test) is an open field test using 2 individual mice that meet for the first time in order to investigate the sociality. The fundamental procedure of the sociality test is the same as that of the open field test using 1 individual member. However, at the time of starting the behavioral observation, mice are placed at the opposing corners of the field and their moving is recorded as moving picture for 10 minutes. This test is intended to evaluate the sociality of mice by measuring frequencies and times of social behaviors such as sniffing, grooming, attack, and tail-rattling between 2 individual members.

Since it is possible to assess the effect on the disorders of interpersonal relation and sociality in autism, the result obtained by combining the open field test and the sociality test is effective in evaluating the effect of a pharmaceutical agent in improving ASD (Silverman, J. L., Yang, M., Lord, C., and Crawley, J. N. (2010). Behavioural phenotyping assays for mouse models of autism. Nat. Rev. Neurosci. 11, 490-502).

Figure 6A:
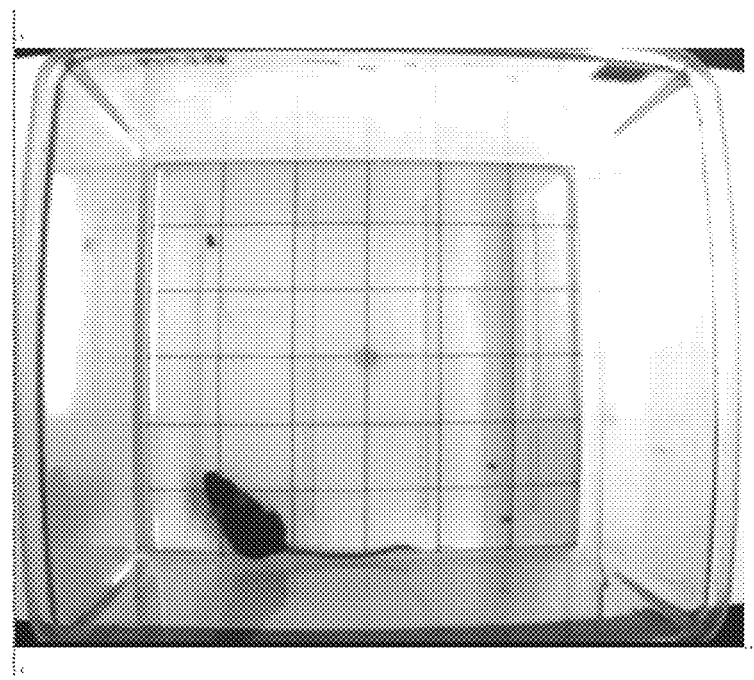
FIG. 6A illustrates how the open field test was conducted on a mouse administered with the agent of the present invention.
Figure 6B:
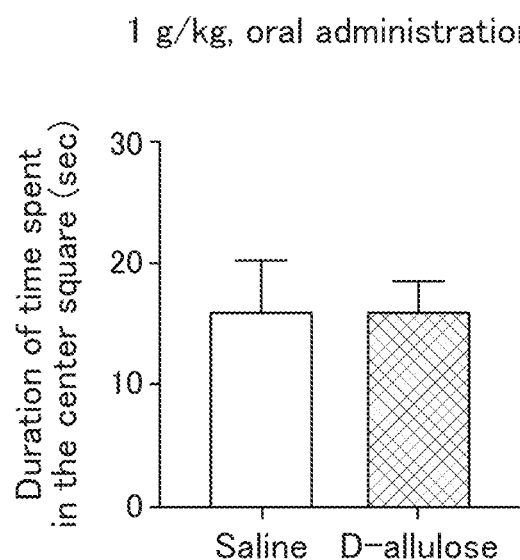
FIG. 6B illustrates results of the open field test on a mouse orally administered with 1 g/kg and 3 g/kg of the agent of the present invention.
Figure 6B:
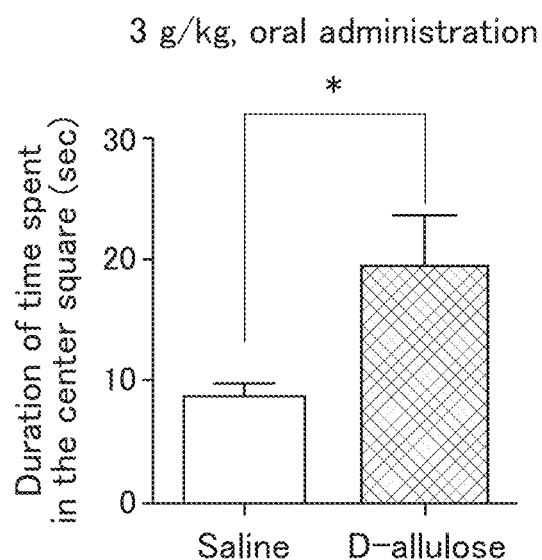
Figure 7A:
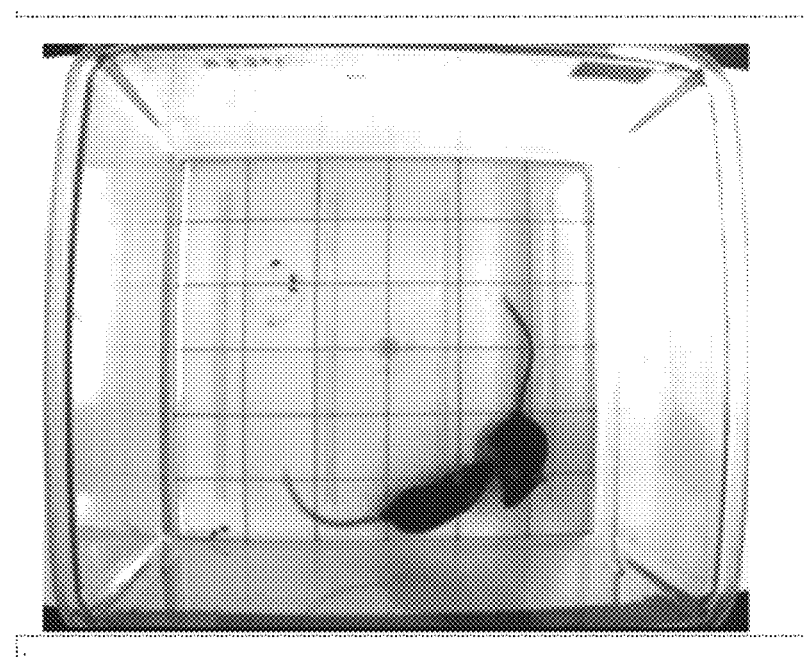
FIG. 7A illustrates how the sociality test was conducted on a mouse administered with the agent of the present invention and a result thereof.

When the open field test and the sociality test were conducted using the pharmaceutical agent of the present invention, the mice administered with the pharmaceutical agent of the present invention showed anxiety significantly reduced as compared with a control mice administered with saline (FIGS. 6A to 6B). In addition, since the sociability was significantly facilitated (FIGS. 7A to 7B), it was suggested that the pharmaceutical agent functions as a pharmaceutical agent for improving ASD.

Activation of Neurons in Hypothalamus

Regarding the effect of improving ASD of the pharmaceutical agent of the present invention, tests to confirm the effect of the pharmaceutical agent of the present invention on the oxytocin neuron and the vasopressin neuron were conducted.

It has been reported that oxytocin, which is known as a posterior pituitary hormone, is synthesized in neuron of the paraventricular nucleus (PVN) and the supraoptic nucleus (SON) of the hypothalamus, and the nerve terminal projects to the posterior pituitary and secreted into the blood to facilitate delivery and milk ejection. Oxytocin also functions as a brain neurotransmission and part of the oxytocin neuron projects into the brain to exert the central nerve function. As the central oxytocin functions, social behavior improvements ((1) Bales et al., "Long-term exposure to intranasal oxytocin administration in a mouse autism model", Transl. Psychiatry 2014; 4:e480, (2) Huang et. al., "Chronic and acute intranasal oxytocin administration produce divergent social effects in mice." Neuropsychopharmacology, 2014; 39: 1102-1114)), anti-anxiety, anti-stress, learning facilitation, anti-obesity effects, and the like have been reported (Meyer-Lindenberg A. et al., Nat Rev Neurosci. 2011, 12(9):524-38, Blevins J E and Baskin D G, Physiol Behav. 2015 152(Pt B):438-49).

Vasopressin is also, like oxytocin, a posterior pituitary hormone synthesized in the paraventricular nucleus and the supraoptic nucleus of the hypothalamus. Vasopressin is also known to be involved in mentation of schizophrenia, autism, and the like, like oxytocin (References: Egashira Nobuaki, et al., Journal of Pharmacological Sciences, 2009, 134, 3-7 and Meyer-Lindenberg A. et al., Nat Rev Neurosci. 2011, 12(9): 524-38). It is considered that one of the reasons why vasopressin has a mentation similar to that of oxytocin is that vasopressin is likely to act on oxytocin receptors in addition to its receptors, that is, vasopressin receptors (V1a, V1b, V2) (Reference: Koshimizu T. et al., Physiol Rev 92: 1813-1864, 2012). In addition, it has been reported that the vasopressin receptors (V1a, V1b) expressed in the center are also involved in mentation of social behavior, depression, anxiety, and the like (Egashira N et al., J Pharmacol Sci. 2009, 109, 44-49).

It is known that orally administering the pharmaceutical agent of the present invention causes information transmission to the brain through the afferent vagal nerve to induce a feeling of fullness and reduce food consumption (Japanese Patent Application Publication No. 2015-164900). However, on which region in the brain the oral administration of the pharmaceutical agent of the present invention acts, particularly the involvement of the hypothalamus, the oxytocin and vasopressin neurons are unknown at all. In view of this, with focus on the hypothalamus involved in sociality, anxiety, stress, learning, intake, and metabolism, the activated region of the hypothalamus by oral administration of the pharmaceutical agent of the present invention was analyzed.

With the oral administration of the pharmaceutical agent of the present invention, the facilitation of expression of c-Fos was observed in the paraventricular nucleus (PVN), supraoptic nucleus (SON), and a new region that was not identified in the atlas present on the ventral side from the ventromedial nucleus, in the hypothalamus (FIGS. 1A to 1D).

Figure 2A:
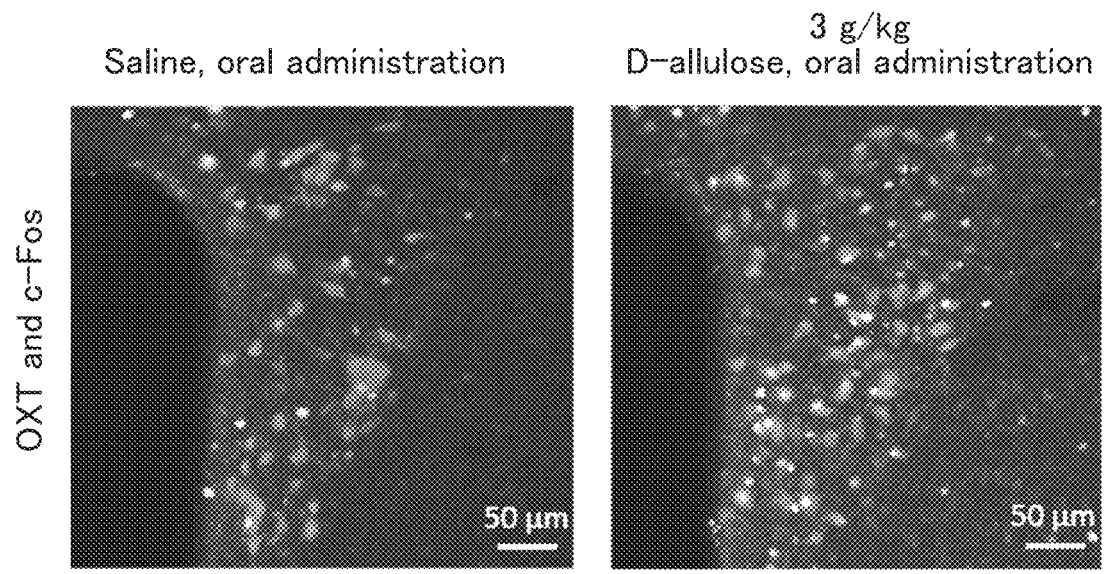
FIG. 2A illustrates that the oral administration of the agent of the present invention activated the oxytocin (OXT) neurons of the paraventricular nucleus (PVN). The portions in which the cytoplasm illuminating in light gray are oxytocin positive cells, and small portions in illuminating in white in the nuclei indicate c-Fos protein expression.
Figure 2B:
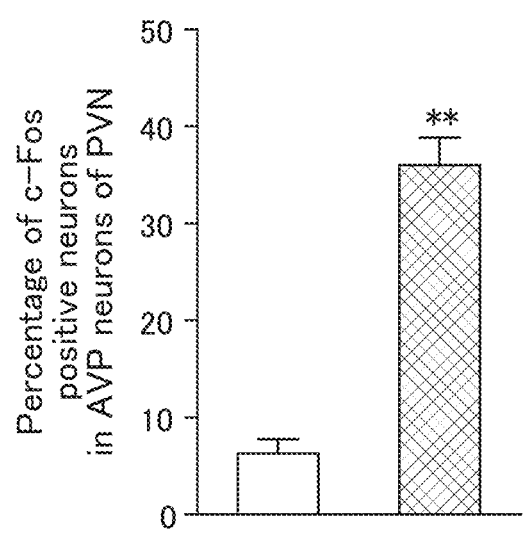
FIG. 2B illustrates a percentage (%) of c-Fos positive neurons in the oxytocin neurons of the paraventricular nucleus (PVN) of the hypothalamus.

It was found that the oral administration of the pharmaceutical agent of the present invention significantly increased the c-Fos expression level to activate in the oxytocin (OXT) neuron of the paraventricular nucleus (PVN) (FIGS. 2A and 2B). In FIG. 2A, light gray portions are oxytocin positive cells, and portions illuminating in white mean the expression of c-Fos protein present in the nuclei of the oxytocin positive cells.

Figure 2C:
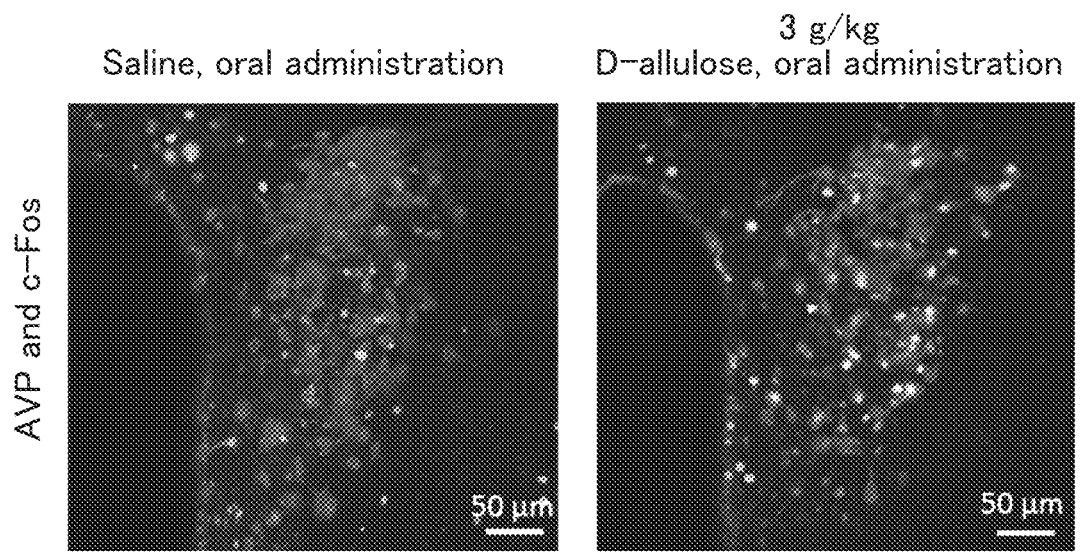
FIG. 2C illustrates that the oral administration of the agent of the present invention activated the vasopressin (AVP) neurons of the paraventricular nucleus (PVN). Portions illuminating in light gray in the entire cytoplasm are vasopressin positive cells, small portions illuminating in white in the nucleus indicate c-Fos protein expression.
Figure 2D:
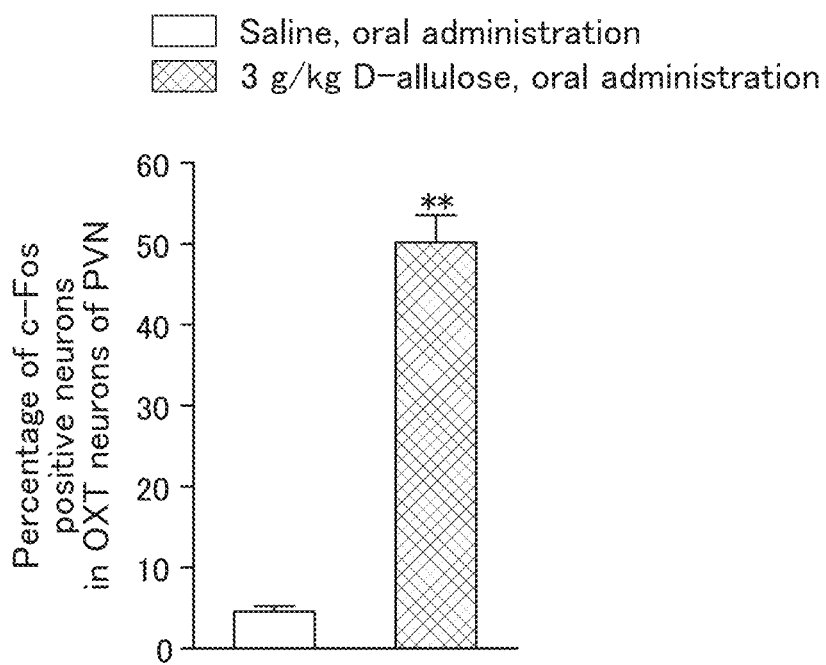
FIG. 2D illustrates a percentage (%) of c-Fos positive neurons in the vasopressin neuron of the paraventricular nucleus (PVN) of the hypothalamus.

Likewise, it was revealed that the oral administration of the pharmaceutical agent of the present invention activated the vasopressin (AVP) neuron of the paraventricular nucleus (PVN) (FIGS. 2C and 2D).

Figure 3A:
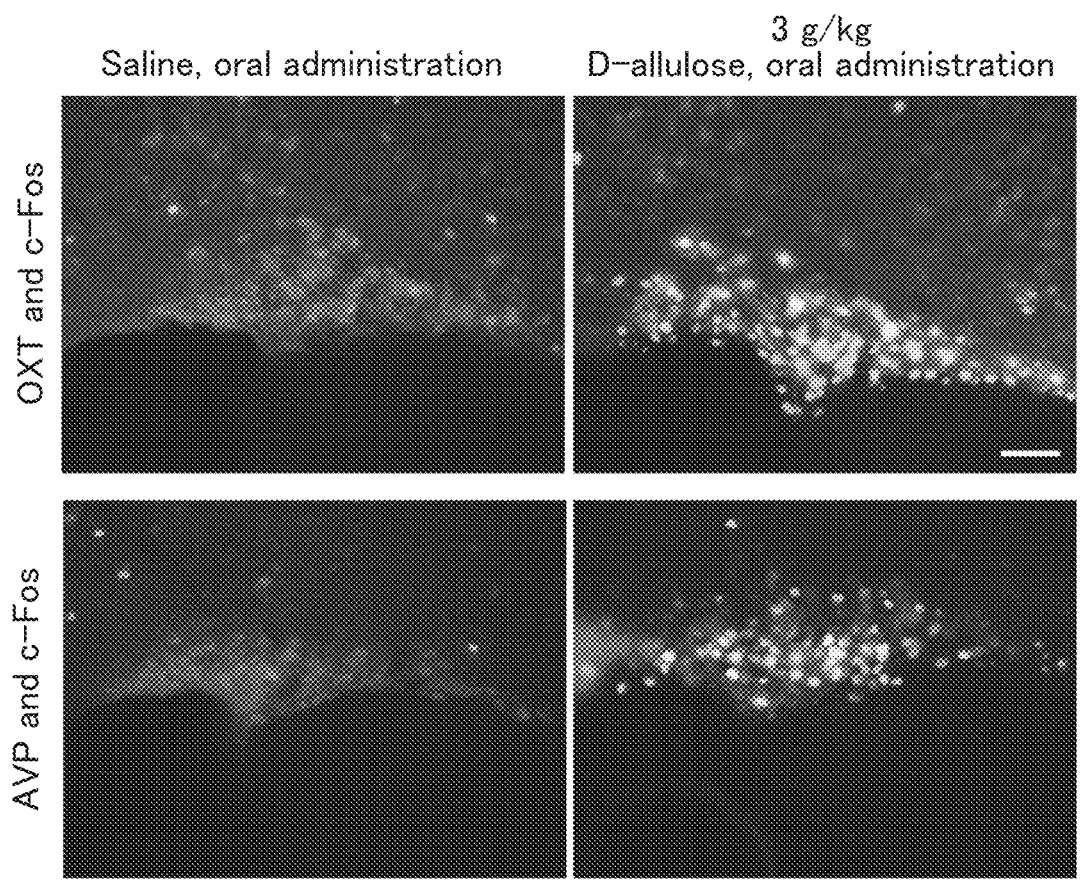
FIG. 3A illustrates that the oxytocin (OXT) and the vasopressin (AVP) neurons of the supraoptic nucleus (SON) of the hypothalamus are activated. Portions illuminating in light gray are oxytocin or vasopressin positive cells, and portions illuminating in white indicate c-Fos protein expression present in the nuclei of the cells.
Figure 3B:
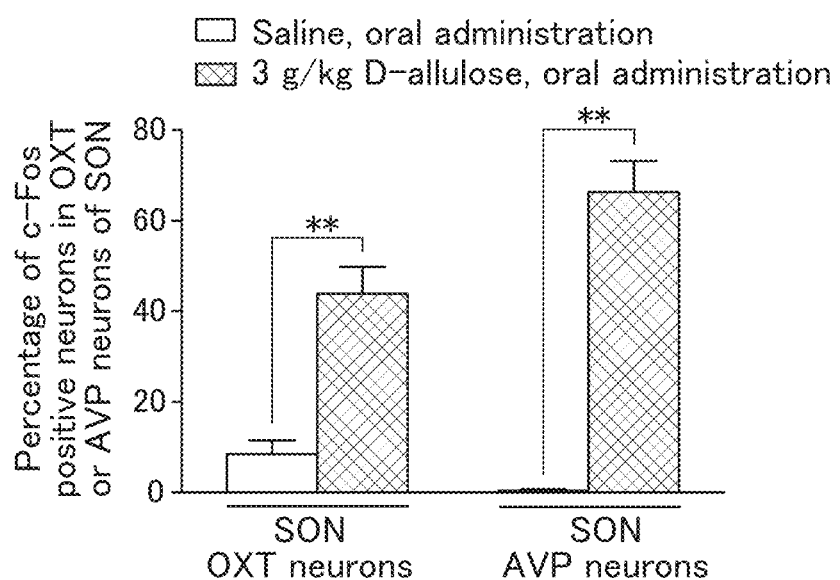
FIG. 3B illustrates a percentage (%) of c-Fos positive neurons in the oxytocin and vasopressin neurons of the supraoptic nucleus (SON) of the hypothalamus.

In addition, it was also revealed that the oral administration of the pharmaceutical agent of the present invention activated the oxytocin and vasopressin neurons of the supraoptic nucleus (SON) (FIGS. 3A and 3B).

Figure 4A:
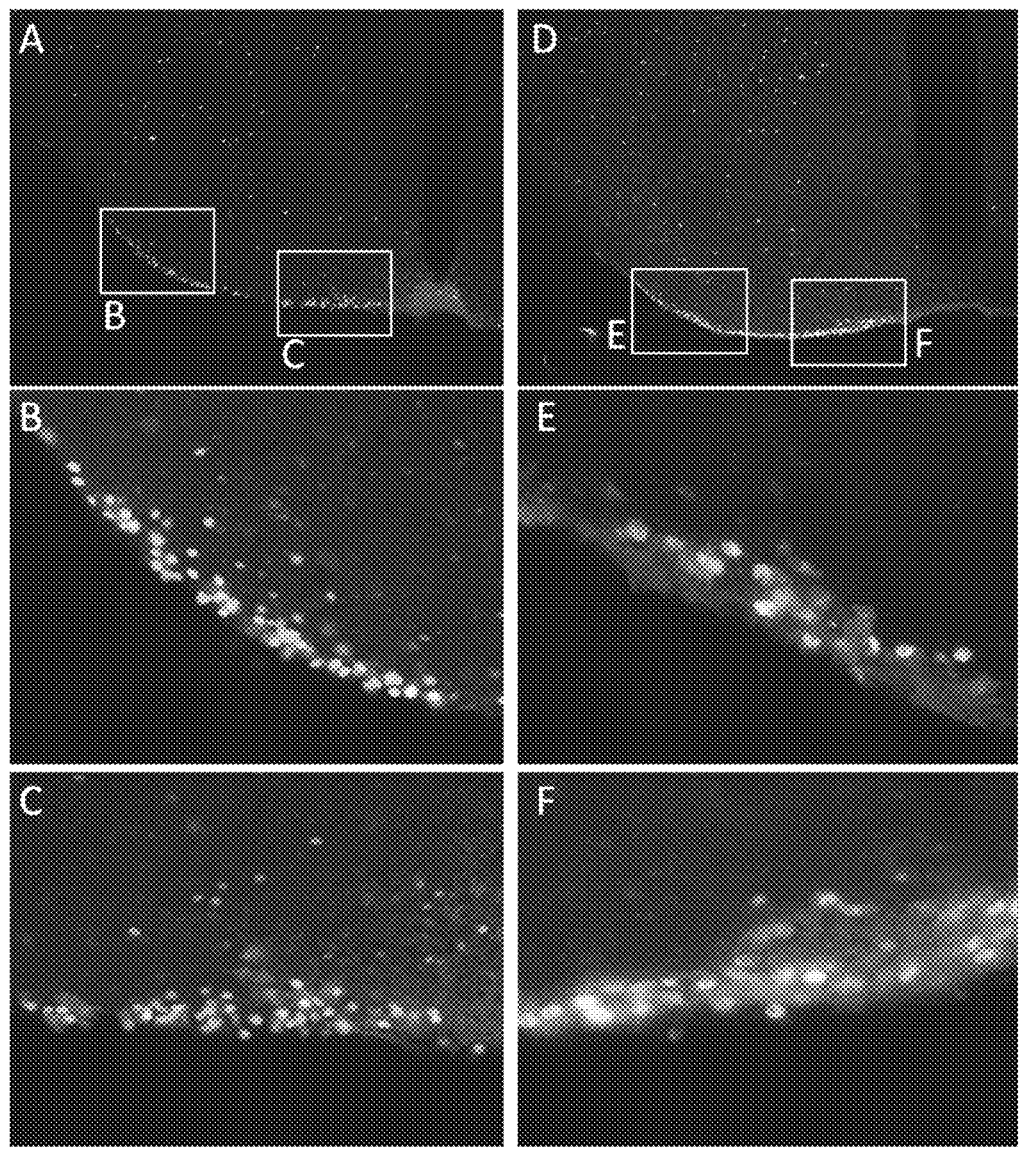
FIG. 4A illustrates that the oxytocin (OXT) (A-C) and vasopressin(AVP) (D-F) neurons of a new region of the hypothalamus are activated. Portions illuminating in light gray are oxytocin or vasopressin positive cells, and portions illuminating in white indicate c-Fos protein expression present in the nuclei of the cells. Enlarged diagrams of B, C in FIG. A are illustrated in FIGS. B, C. In addition, enlarged diagrams of E, F in FIG. D are illustrated in FIGS. E, F.
Figure 4B:
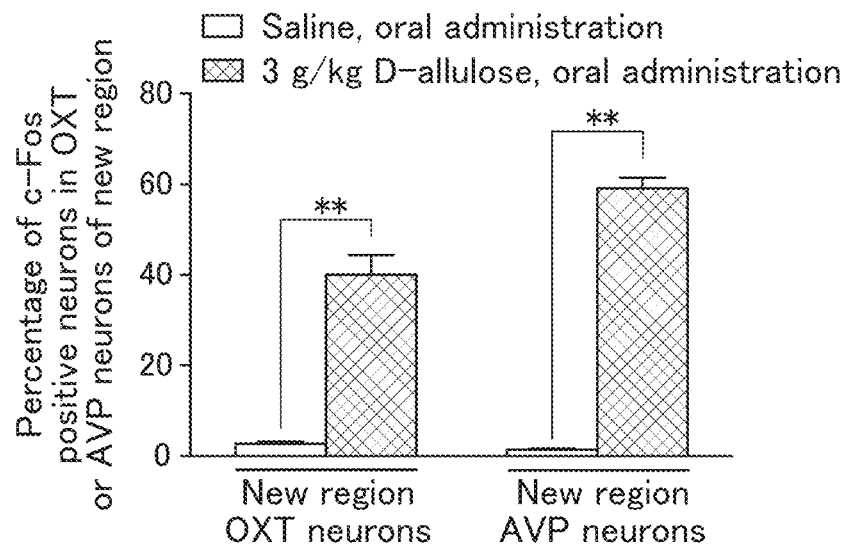
FIG. 4B illustrates a percentage (%) of c-Fos positive neurons in the oxytocin and vasopressin neurons in the new region of the hypothalamus.

Regarding the new region in the hypothalamus, which was activated by the oral administration of the pharmaceutical agent of the present invention, it was first found that the oxytocin and vasopressin neurons were present with a high frequency. Then, it was found that the oral administration of the pharmaceutical agent of the present invention activated the oxytocin and vasopressin neurons in this new region (FIGS. 4A and 4B).

Enhancement of Expression of Oxytocin/Vasopressin mRNAs in Hypothalamus

Figure 5:
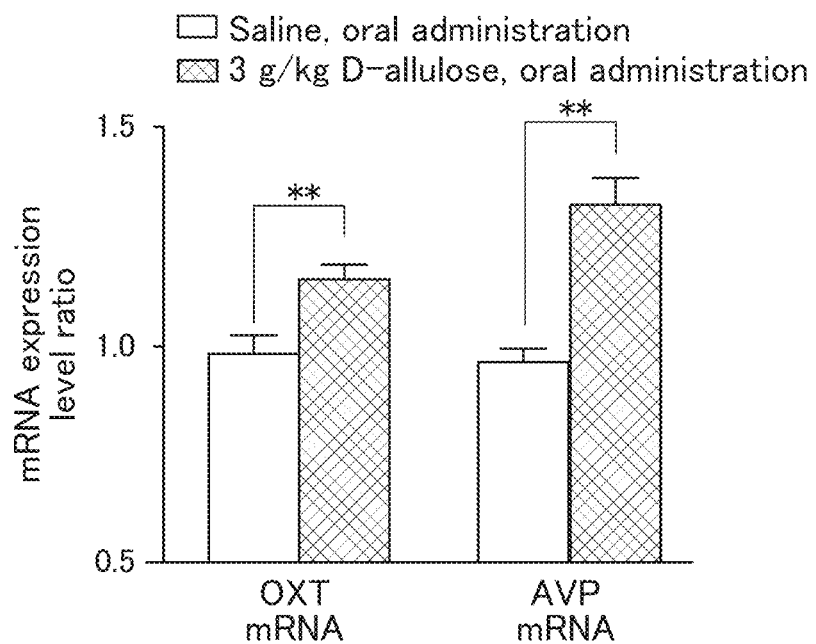
FIG. 5 illustrates a change in expression level of the oxytocin and vasopressin mRNAs in the hypothalamus of a mouse administered with the agent of the present invention.

It was revealed that the oral administration of the pharmaceutical agent of the present invention significantly enhanced the expression of the mRNAs of oxytocin and vasopressin in the hypothalamus as compared with the control (saline-administered group) (FIG. 5). That is, it is considered that the oral administration of the pharmaceutical agent of the present invention facilitates the gene expression of oxytocin and vasopressin in the hypothalamus, which promotes the synthesis of oxytocin and vasopressin, serving as a factor for an increase in secretion volumes.

As shown in FIGS. 1 to 4, facilitation of the gene expression of oxytocin and vasopressin was observed in the paraventricular nucleus (PVN), the supraoptic nucleus (SON), and the new region in the hypothalamus. It is considered that the initial activation of neurons (expression of c-Fos) might have promoted the gene expression of oxytocin and vasopressin and the protein synthesis.

The effect of improving ASD of the pharmaceutical agent of the present invention observed in the open field test and the social interaction test is surmised to be based on the effect of activating the oxytocin and vasopressin neurons in the hypothalamus and the effect of enhancing the expression of oxytocin and vasopressin mRNAs, which the pharmaceutical agent of the present invention has.

From the above, the present invention provides a pharmaceutical agent for promoting the secretion of oxytocin and/or vasopressin, which is a pharmaceutical agent for promoting the secretion of oxytocin and/or vasopressin, preferably in the brain, further preferably in the brain of a mammal, and particularly in the brain of a human.

Pharmaceutical Agent for Treating Mental Disease

Another aspect of the present invention is a pharmaceutical agent for treating a mental disease comprising D-allulose as an active ingredient.

As described above, the pharmaceutical agent of the present invention exhibited results of facilitating anti-anxiety and sociality in the open field test and the sociality test, and acts on central oxytocin. This suggests that the pharmaceutical agent of the present invention can be used also as a therapeutic agent for another mental disease to which oxytocin activation relates.

That is, it is obvious that mental diseases in which central oxytocin is considered to be involved, such as social anxiety disorder, borderline personality disorder, schizophrenia, and memory impairment, may be more effectively improved by the pharmaceutical agent of the present invention.

Anti-Anxiety Agent, Anti-Stress Agent, Anxiety-Reducing Food, and Stress-Reducing Food Still another aspect of the present invention is an anti-anxiety agent or anti-stress agent comprising D-allulose as an active ingredient.

Another aspect of the present invention is an anxiety-reducing food or stress-reducing food comprising D-allulose as an active ingredient.

In embodiments of the present invention, the term during which a disease is improved or mitigated is not particularly limited, but the improvement or mitigation may be a temporal improvement or mitigation, or improvement or mitigation for a certain period of time.

Although the present invention is described in further detail using Examples, the present invention is not limited by Examples at all.

EXAMPLES

Example 1: Analysis of Activated Regions in Afferent Vagal Nerve and Brain in Oral Administration of D-Allulose For brain regions that are activated by the oral administration of D-allulose, the expression levels of a neuronal activation marker (c-Fos) were analyzed by the immunostaining method. c-Fos is one of immediate early genes, is a nuclear protein whose expression level increases along with activation of nerves, and thus can be utilized as a neuronal activation marker.

C57BL/6J male mice were used as experimental animals and were acclimatized to an environment through preliminary breeding and handling for 1 week or more in individual cages. Saline or D-allulose (1 or 3 g/kg) was orally intragastrically administered to the mice which were fasted for one night, and 90 minutes after the administration, the mice were perfusion fixed in a 4% paraformaldehyde solution and the brains were resected. The organs were postfixed in a 4% paraformaldehyde solution to prepare frozen section specimens. This frozen section specimen was used to immunostain c-Fos. In the case of double immunostaining for oxytocin/vasopressin and c-Fos, the perfusion fixation and the postfixation were conducted in a mixed solution of 4% paraformaldehyde and 0.2% picric acid.

The obtained results are shown in FIGS. 1 to 4.

Note that in the experiment for analyzing c-FOS expression level (FIG. 1A to FIG. 1D), C57BL/6J male mice of saline group: n=7, 1 g/kg and 3 g/kg D-allulose group: n=5 each were used.

In the experiment for analyzing c-Fos positive neurons in the oxytocin (OXT) neurons of paraventricular nucleus (PVN) (FIG. 2A and FIG. 2B), C57BL/6J male mice of saline group: n=4, 3 g/kg D-allulose group: n=6 were used.

In the experiment for analyzing c-Fos positive neurons in the vasopressin (AVP) neurons of paraventricular nucleus (PVN) (FIG. 2C and FIG. 2D), C57BL/6J male mice of saline group: n=4, 3 g/kg D-allulose group: n=6 were used. In the experiment for analyzing c-Fos positive neurons in the oxytocin (OXT) neurons or vasopressin (AVP) neurons of paraventricular nucleus (PVN) (FIG. 3A and FIG. 3B), C57BL/6J male mice of saline group n=4, 3 g/kg D-allulose group: n=6 were used.

In the experiment for analyzing c-Fos positive neurons in the oxytocin (OXT) neurons or vasopressin (AVP) neurons of the new region (FIG. 4A and FIG. 4B), C57BL/6J male mice of saline group: n=4, 3 g/kg D-allulose group: n=6 were used.

The obtained results are represented by the average values and the standard errors, the statistical testing used the unpaired t-test, * is described by the P value of less than 5% and ** is described by the P value of less than 1%.
(In the statistical testing, after the analysis using the one-way analysis of variance, the Dunnett's test was conducted on the control group, and * is described by the P value of less than 5% and ** is described by the P value of less than 1%.)

Example 2: Analysis of Change in Expression Level of Oxytocin/Vasopressin mRNAs in Hypothalamus after Oral Administration of D-Allulose C57BL/6J male mice (saline group: n=8, D-allulose group: n=9) were used as experimental animals and were acclimatized to an environment through preliminary breeding and handling for 1 week or more in individual cages. Saline or D-allulose (3 g/kg) was orally intragastrically administered to the mice which were fasted for one night, and 2 hours after the administration, the brain's hypothalamus was resected under anesthesia. cDNA was synthesized using the total RNA in hypothalamus as a template. The mRNA expression levels of oxytocin and vasopressin were quantified by the quantitative real-time PCR method. As the housekeeping gene, 36b4 was used. The mRNA expression levels were quantified in accordance with the ΔΔCt method. The target gene expression level in each sample was corrected with the expression level of 36b4 to obtain the relative expression level to 36b4 (ΔCT=the CT value of 36b4−the CT value of the target gene, the relative expression level=2ΔCT).

Moreover, the mRNA expression level ratio with the average value of the relative expression level of the saline group being set to 1 (the average value of the relative gene expression level of the D-allulose group to 36b4/the average value of the relative expression level of the saline group to 36b4) was obtained to analyze the change in gene expression level in the administration of D-allulose.

The obtained results are shown in FIG. 5.

The obtained results are represented by the average values and the standard errors, the statistical testing used the unpaired t-test, and ** is described by the P value of less than 1%.

Example 3: Behavioral Test

Animals

C57BL/6J male mice (8-week old) were bred for 1 week under a free-feeding condition with a light-dark cycle of 12 hours and were subjected to the open field and sociality tests. Handling and gavage training was conducted for 4 days before the test.

Open Field Test

D-allulose (1 g/kg or 3 g/kg) or saline was orally administered 30 minutes before the start of the test. In order to evaluate the anxiety behavior against the novel environment, each mouse was allowed to explore in a new breeding cage (27×27×20 cm$^3$). The duration of time spent in the center square (9×9 cm$^3$) during an exploratory behavior time of 5 minutes was measured. It was conducted with n=10, and as shown in FIG. 6B, although there was no significant result for 1 g/kg, it was indicated that the anxiety behavior was significantly improved for 3 g/kg as compared with the saline-administered group ($p<0.05$ ($_{t\text{-}test}$)).

Sociality Test

Figure 7B:
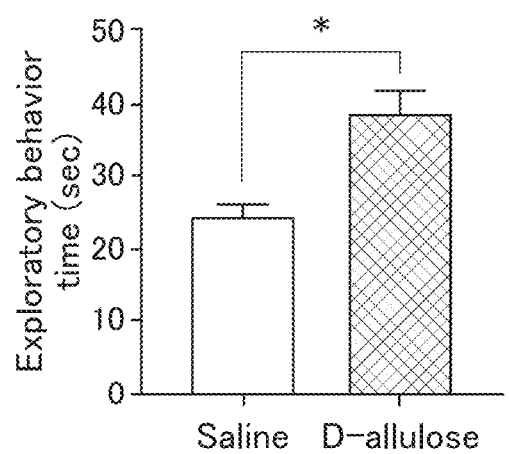
FIG. 7B illustrates results (exploratory behavior time) of the sociality test on a mouse orally administered with 1 g/kg and 3 g/kg of the agent of the present invention.
Figure 7B:
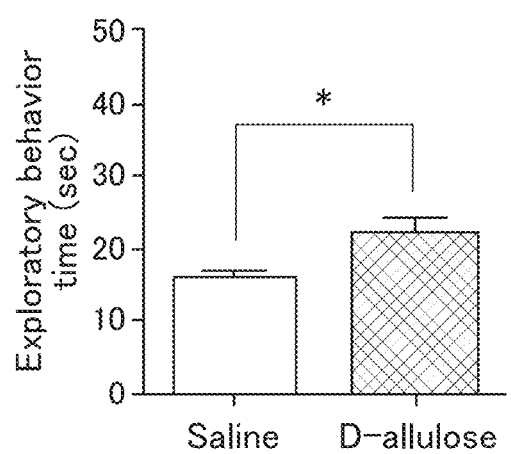

In order to evaluate the sociality with a same-sex mouse, each mouse was placed together with a mouse (new mouse) which it met for the first time in a breeding cage (27×27×20 cm$^3$) and an accumulation time of the exploratory behavior against the new mouse during an exploratory behavior time of 10 minutes was measured. It was conducted with n=10, and as shown in FIG. 7B, it was shown that the social behavior was significantly facilitated in both tests of 1 g/kg and 3 g/kg as compared with the saline-administered group ($p<0.05$ ($_{t\text{-}test}$)).

As a result of the open field test, the exploratory behavior time for the D-allulose-administered group is significantly extended as compared with the saline-administered group. Therefore, the administration of D-allulose is considered to have a mitigation effect for novel environment anxieties.

As a result of the sociality test, the administration of D-allulose exhibited an increase in accumulated exploratory behavior time of the exploratory behavior against the new mouse. Therefore, D-allulose is considered to act on the facilitation of social behaviors.

What is claimed is:

1. A method of treating or improving one or more of the following diseases and symptoms in a human subject in need thereof:
    (i) diseases selected from the group consisting of autism spectrum disorder and mental diseases in which central oxytocin is considered to be involved, and
    (ii) symptoms selected from the group consisting of social behavior disorders, anxiety disorders, and stresses,
    the method comprising
    administering to the subject a composition including a therapeutically-effective amount of D-allulose as an active ingredient,
    and thereby treating or improving the one or more diseases and symptoms,
    wherein the composition is administered at a dose that includes about 0.007 g to 0.5 g D-allulose per 1 kg body weight of the subject.

2. The method of claim 1, wherein the administration of the composition including the D-allulose effectively improves a mental disease of the subject.

3. The method of claim 1, wherein the administration of the composition including the D-allulose effectively improves social behaviors of the subject.

4. The method of claim 1, wherein the administration of the composition including the D-allulose effectively treats or improves the subject's anxiety.

5. The method of claim 1, wherein the administration of the composition including the D-allulose effectively treats stress for the subject.

6. The method of claim 1, wherein the composition including the D-allulose is administered in the form of a food, as an anxiety-reducing treatment for the subject.

7. The method of claim 1, wherein the composition including the D-allulose is administered in the form of a food, as a stress-reducing treatment for the subject.

8. The method of claim 1, wherein the composition including the D-allulose effectively promotes the secretion of oxytocin, vasopressin, or both oxytocin and vasopressin in the subject.

9. The method of claim 2, wherein the composition including the D-allulose is administered orally and effectively promotes secretion of oxytocin, vasopressin, or both oxytocin and vasopressin in the subject's brain, thereby treating a mental disease.

10. The method of claim 1, wherein the composition including the D-allulose is orally administered.

11. The method of claim 1, wherein the composition including the D-allulose is administered to treat or improve the one or more diseases and symptoms in the subject by promoting the secretion of oxytocin and/or vasopressin in the subject's brain.

12. The method of claim 1, wherein the composition including the D-allulose is administered to improve autism spectrum disorder in the subject.

13. The method of claim 12, wherein the composition including the D-allulose is administered orally to the subject to promote the secretion of oxytocin, vasopressin, or both oxytocin and vasopressin in the subject's brain, improving autism spectrum disorder in the subject.

14. The method of claim 11, wherein the composition including the D-allulose is administered orally to the subject.

15. The method of claim 1, wherein the disease in (i) is a mental disease selected from the group consisting of social anxiety disorder, borderline personality disorder, and schizophrenia.

16. The method of claim 1, wherein the disease in (i) is autism spectrum disorder.

17. The method of claim 1, wherein the D-allulose is administered to the subject as the sole active ingredient.

18. The method of claim 1, wherein the composition including the D-allulose is administered at a dose that includes 0.12 g to 0.35 g D-allulose per 1 kg of body weight.

19. The method of claim 1, wherein the composition including the D-allulose is administered at a dose of 10 g to 12 g D-allulose.

20. The method of claim 1, further comprising, before the administering step, a step of determining that the subject has one or more of the diseases and symptoms.

* * * * *